US012767653B2

(12) United States Patent
Šagud et al.

(10) Patent No.: US 12,767,653 B2
(45) Date of Patent: Oct. 20, 2026

(54) PROCESS FOR PREPARATION OF SOTORASIB AND SOLID STATE FORM THEREOF

(71) Applicant: ASSIA CHEMICAL INDUSTRIES LTD., Tel Aviv (IL)

(72) Inventors: Ivana Šagud, Gornja Stubica (HR); Lorena Kordić, Rab (HR); Moris Mihovilovic, Zagreb (HR); Irena Nekola, Sisak (HR)

(73) Assignee: ASSIA CHEMICAL INDUSTRIES LTD., Tel Aviv (IL)

( * ) Notice: Subject to any disclaimer, the term of this patent is extended or adjusted under 35 U.S.C. 154(b) by 372 days.

(21) Appl. No.: 18/561,845

(22) PCT Filed: May 19, 2022

(86) PCT No.: PCT/US2022/030035
§ 371 (c)(1),
(2) Date: Nov. 17, 2023

(87) PCT Pub. No.: WO2022/246069
PCT Pub. Date: Nov. 24, 2022

(65) Prior Publication Data

US 2024/0254122 A1 Aug. 1, 2024

Related U.S. Application Data

(60) Provisional application No. 63/295,971, filed on Jan. 3, 2022, provisional application No. 63/190,315, filed on May 19, 2021.

(51) Int. Cl.
*C07D 471/04* (2006.01)
*A61K 31/519* (2006.01)

(52) U.S. Cl.
CPC .......... *C07D 471/04* (2013.01); *A61K 31/519* (2013.01)

(58) Field of Classification Search
CPC ............................ C07D 471/04; A61K 31/519
USPC ..................................................... 514/252.16
See application file for complete search history.

(56) References Cited

U.S. PATENT DOCUMENTS

| | | | |
|---|---|---|---|
| 10,519,146 | B2 | 12/2019 | Lanman et al. |
| 11,236,091 | B2 | 2/2022 | Chaves et al. |
| 11,827,635 | B2 | 11/2023 | Chaves et al. |
| 2018/0334454 | A1 | 11/2018 | Lanman et al. |
| 2020/0369662 | A1 | 11/2020 | Chaves et al. |

FOREIGN PATENT DOCUMENTS

| | | | |
|---|---|---|---|
| JP | 2023544775 | A | 10/2023 |
| WO | 2018217651 | A1 | 11/2018 |
| WO | 2020102730 | A1 | 5/2020 |
| WO | 2020236947 | A1 | 11/2020 |
| WO | 2020236948 | A1 | 11/2020 |
| WO | 2020259513 | A1 | 12/2020 |
| WO | 2021121330 | A1 | 6/2021 |
| WO | 2021236920 | A1 | 11/2021 |
| WO | 2022076623 | A1 | 4/2022 |

OTHER PUBLICATIONS

Brian A. Lanman, et al., "Discovery of a Covalent Inhibitor of KRASG12C (AMG 510) for the Treatment of Solid Tumors", J. Med. Chem. 2020, 63, 52-65.
Kazuhide Ashizawa, The Chemistry of Polymorphism and Crystallization of the Pharmaceutical Drugs, 2002, pp. 273, 278, 305-17 (English translation not available. Statement of Relevance can be found in the attached IDS Transmittal Letter.).
Office Action issued in corresponding Japanese Application No. 2023-571685 mailed Dec. 2, 2025, together with English language translation.
Pharmacia, 2016, vol. 52, No. 5, pp. 387-391 (English translation not available. Statement of Relevance can be found in the attached IDS Transmittal Letter.).
Communication pursuant to Rule 114(2) EPC issued in corresponding application 22729966.6 dated Apr. 8, 2024 (3 pages).
International Search Report and Written Opinion of the International Searching Authority issued in corresponding application PCT/US2022/030035 mailed Oct. 17, 2022 (13 pages).
U.S. Pat. No. 11,827,635 B2 with appended priority document (U.S. Appl. No. 62/851,044) (Year: 2019).

*Primary Examiner* — Kristin A Vajda
(74) *Attorney, Agent, or Firm* — Carter, DeLuca & Farrell LLP

(57) ABSTRACT

The present disclosure relates to a process for the preparation of Sotorasib and salts thereof useful as a pharmaceutical active compound. The present disclosure also relates to intermediates for the preparation of Sotorasib and salts thereof. Further, the present disclosure encompasses solid state forms of Sotorasib, in embodiments crystalline polymorphs of Sotorasib, processes for preparation thereof, and pharmaceutical compositions thereof. Also provided are processes for the preparation of Sotorasib.

14 Claims, 1 Drawing Sheet

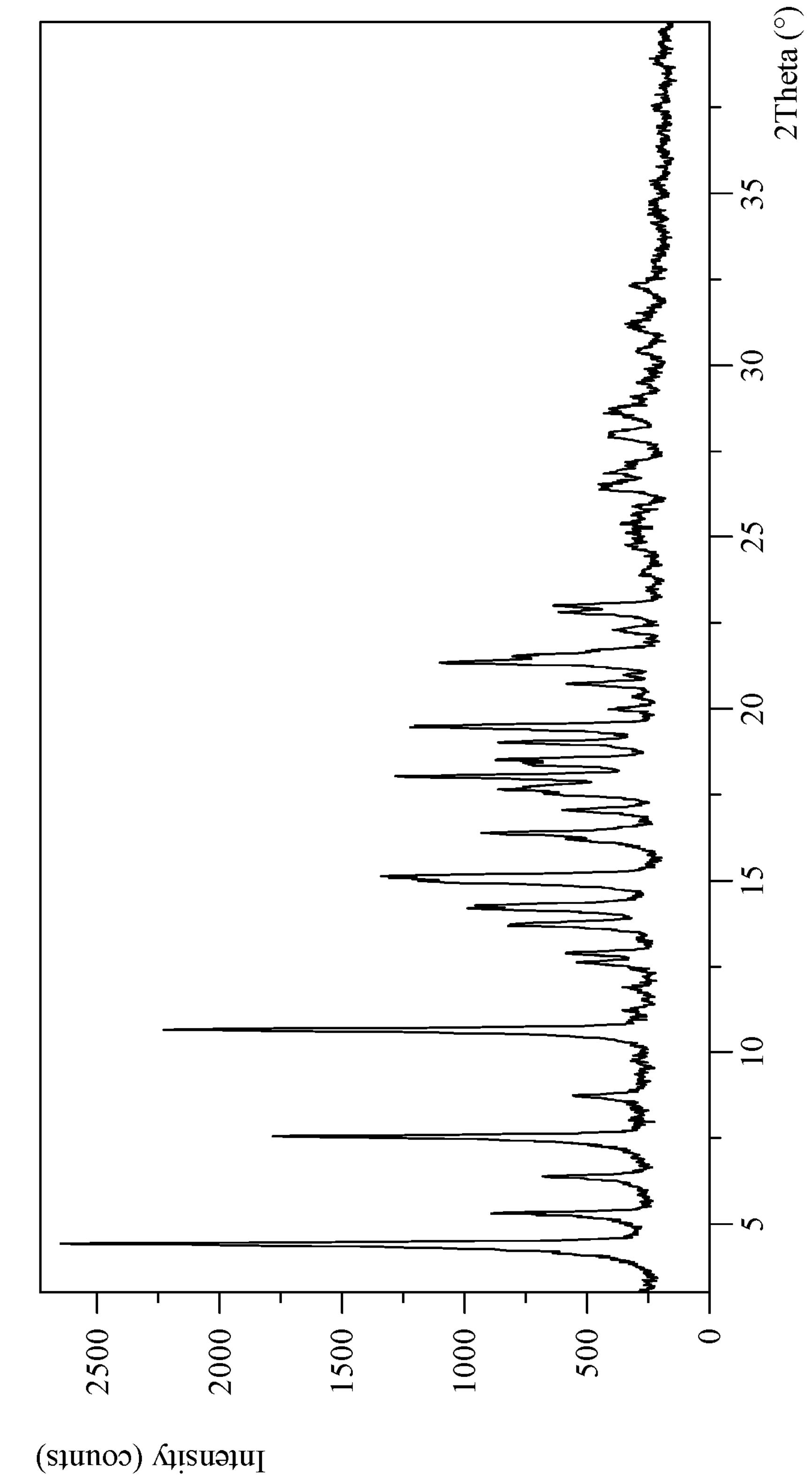
XRPD pattern of Sotorasib, Form H5

PROCESS FOR PREPARATION OF SOTORASIB AND SOLID STATE FORM THEREOF

CROSS REFERENCE TO RELATED APPLICATIONS

This application is a National Stage of, and claims priority to and the benefit of, International Patent Application No. PCT/US2022/030035, filed May 19, 2022, which, in turn, claims the benefit of and priority to, U.S. Provisional Application No. 63/190,315, filed on May 19, 2021 and U.S. Provisional Application No. 63/295,971 filed on Jan. 3, 2022, the entire disclosures of each of which are incorporated by reference herein.

FIELD OF THE INVENTION

The present disclosure relates to a process for the preparation of Sotorasib and salts thereof useful as a pharmaceutical active compound. The present disclosure also relates to intermediates for the preparation of Sotorasib and salts thereof. Further, the present disclosure encompasses solid state forms of Sotorasib, in embodiments crystalline polymorphs of Sotorasib, processes for preparation thereof, and pharmaceutical compositions thereof. Also provided are processes for the preparation of Sotorasib.

BACKGROUND OF THE INVENTION

Sotorasib has the chemical name 4-((S)-4-acryloyl-2-methylpiperazin-1-yl)-6-fluoro-7-(2-fluoro-6-hydroxyphenyl)-1-(2-isopropyl-4-methylpyridin-3-yl) pyrido [2,3-d] pyrimidin-2(1H)-one and the following chemical structure:

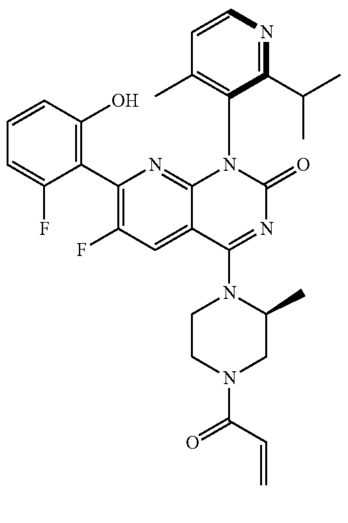

Sotorasib is described in International Publication No. WO 2018/217651 as a compound which belongs to KRAS G12C inhibitors. KRAS gene mutations are reported to be common in pancreatic cancer, lung adenocarcinoma, colorectal cancer, gall bladder cancer, thyroid cancer and bile duct cancer.

Apparently, KRAS mutations are also observed in about 25% of patients with NSCLC (Non-small cell lung cancer), and some studies have indicated that KRAS mutations are a negative prognostic factor in patients with NSCLC.

The compound is described in U.S. Pat. No. 10,519,146 and solid state forms are described in U.S. Pat. No. 11,236, 091.

As disclosed in J. Med. Chem., 2020, 63, 52-65, the compound Sotorasib (AMG 510) exists as conformational isomers (atropisomers) due to hindered rotation about the bis-ortho-substituted biaryl bond). The atropisomers may be designated as the (M)-atropisomer and the (P)-atropisomer. The (M)-atropisomer is generally considered to be the more active isomer.

Solid state forms of Sotorasib and salts thereof are described in International Publication Nos. WO2020236947, WO2020236948 and WO2021236920.

International Publication No. WO 2018/217651 suggests a process for the preparation of Sotorasib (Compound I), in which they use KF, a corrosive chemical in the preparatory step for the preparation of trifluoro (2-fluoro-6-hydroxyphenyl) borate potassium salt, Scheme I.

Scheme I.

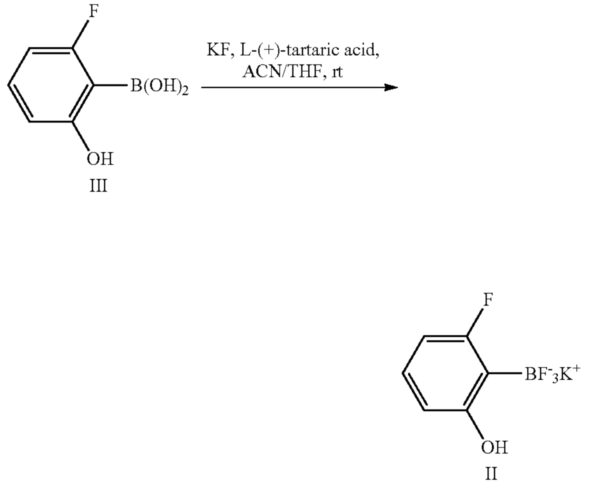

III

II

The same publication also suggests that in the last step for the preparation of Sotorasib from (3S)-tert-butyl 4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-3-methylpiperazine-1-carboxylate (Compound IV) acryloyl chloride be used (Scheme II).

Scheme II

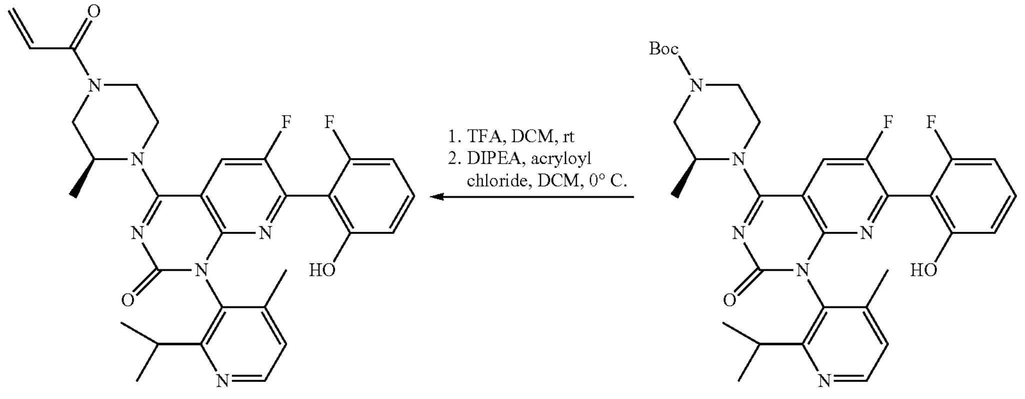

I

IV

International Publication No. WO 2020/102730A1 discloses preparation of Sotorasib with atropoisomer separation in the point of 7-chloro-6-fluoro-1-(2-isopropyl-4-methylpyridin-3-yl) pyrido [2,3-d] pyrimidine-2,4(1H,3H)-dione (compound M-dione V) after neutralization of the cocrystal of compound VI. Co-crystallization is obtained between the THF solvate of Compound VI with (+)-2,3-dibenzoyl-D-tartaric acid.

-continued

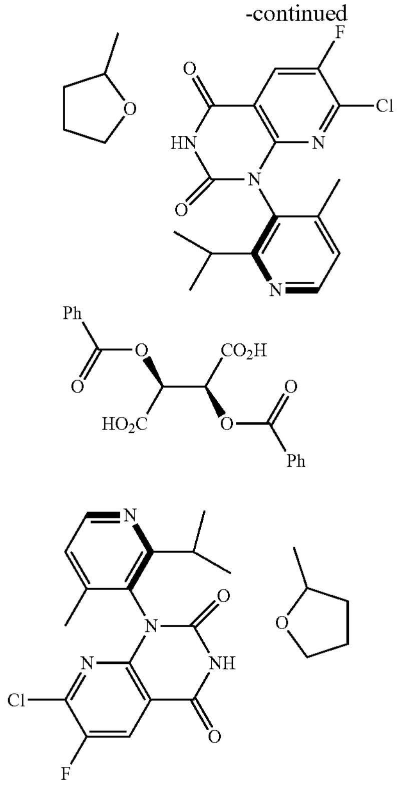

VI DBTA cocrystal

Scheme III

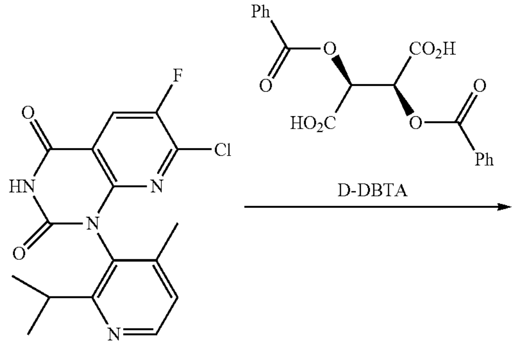

rac-VI

International Publication WO 2022/076623 discloses a process for racemization of 7-chloro-6-fluoro-1-(2-isopropyl-4-methylpyridin-3-yl)pyrido[2,3-d]pyrimidine-2,4(1H, 3H)-dione (Compound VI in Scheme III).

Polymorphism, the occurrence of different crystalline forms, is a property of some molecules and molecular complexes. A single molecule may give rise to a variety of polymorphs having distinct crystal structures and physical properties like melting point, thermal behaviors (e.g., measured by thermogravimetric analysis ("TGA"), or differential scanning calorimetry ("DSC")), X-ray diffraction (XRD) pattern, infrared absorption fingerprint, and solid state ($^{13}C$)

NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, including a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Sotorasib.

The present invention relates to solid state form of Sotorasib. Further, the present invention relates to an improved process for the preparation and atropoisomeric separation of key intermediates in the process of making of Sotorasib and salts thereof. The process gives two possible paths to Sotorasib. The process of the present invention avoids the use of acryloyl chloride, a very unstable chemical that reacts violently with water, sensitive to light and highly flammable.

SUMMARY OF THE INVENTION

The present disclosure provides a process for the preparation of Sotorasib and salts thereof.

The disclosure further provides intermediates and process for the separation of their atropoisomers by making salts, cocrystals or any other polymorphs.

In another aspect the present disclosure provides the use of any one of the intermediates according to the present disclosure for the preparation of Sotorasib.

In another aspect the disclosure provides Sotorasib produced by the processes of the present disclosure.

Sotorasib or Sotorasib salts, cocrystals or other polymorphs produced by the process of the present disclosure may be used in the preparation of pharmaceutical compositions and/or formulations of Sotorasib or Sotorasib salts.

The present disclosure also provides methods of treatment of NSCLC, comprising administrating a therapeutically effective amount of Sotorasib or salts thereof prepared by the process of the present disclosure, to a subject in need of the treatment. In embodiments, Sotorasib or salts thereof prepared by the process of the present disclosure and the pharmaceutical compositions and/or formulations of the present disclosure may be used in the treatment of KRAS G12C-mutant tumors; particularly KRAS G12C-mutant solid tumors; particularly non-small-cell lung cancer, colorectal cancer, pancreatic cancer, appendiceal cancer, endometrial cancer, and melanoma; more particularly in the treatment of non-small-cell lung cancer or colorectal cancer; or in the treatment of advanced or metastatic non-small-cell lung cancer or colorectal cancer, and more particularly locally advanced or metastatic non-small-cell lung cancer or colorectal cancer, and especially in the treatment of advanced or metastatic non-small-cell lung cancer or colorectal cancer following at least one prior systemic therapy.

The present disclosure further provides solid state forms of Sotorasib and salts thereof, in embodiments crystalline polymorphs of Sotorasib, cocrystals of Sotorasib processes for preparation thereof, and pharmaceutical compositions thereof. These solid state forms can be used to prepare other solid state forms of Sotorasib, Sotorasib salts and their solid state forms.

The present disclosure also provides uses of the said solid state forms of Sotorasib in the preparation of other solid state forms of Sotorasib or salts thereof.

The present disclosure provides solid state forms of Sotorasib for use in medicine, including for the treatment of cancer, in particular non-small cell lung and/or colorectal cancers.

The present disclosure also encompasses the use of solid state forms of Sotorasib of the present disclosure for the preparation of pharmaceutical compositions and/or formulations.

In another aspect, the present disclosure provides pharmaceutical compositions comprising solid state forms of Sotorasib according to the present disclosure.

The present disclosure includes processes for preparing the above mentioned pharmaceutical compositions. The processes include combining any one or a combination of the solid state forms of Sotorasib with at least one pharmaceutically acceptable excipient.

The solid state forms of Sotorasib as defined herein and the pharmaceutical compositions or formulations of the solid state forms of Sotorasib may be used as medicaments, such as for the treatment of cancer, in particular non-small cell lung and/or colorectal cancers.

The present disclosure also provides methods of treating cancer, in particular non-small cell lung and/or colorectal cancers, by administering a therapeutically effective amount of any one or a combination of the solid state forms of Sotorasib of the present disclosure, or at least one of the above pharmaceutical compositions, to a subject suffering from non-small cell lung and/or colorectal cancers, or otherwise in need of the treatment.

The present disclosure also provides uses of the solid state forms of Sotorasib of the present disclosure, or at least one of the above pharmaceutical compositions, for the manufacture of medicaments for treating cancer e.g., non-small cell lung and/or colorectal cancers.

BRIEF DESCRIPTION OF THE DRAWINGS

FIG. 1 shows a characteristic X-ray powder diffraction (XRPD) pattern of Sotorasib Form H5.

DETAILED DESCRIPTION OF THE INVENTION

In one aspect the invention provides a process for preparation of Sotorasib and salts thereof. The disclosed process comprising:

a) reacting compound of formula VI rac-VI

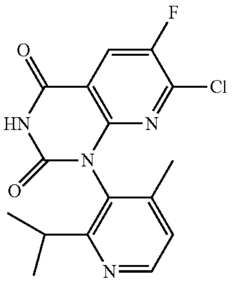

with a compound of formula VIII

VIII

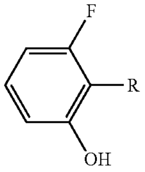

Wherein R is a $B(OH)_2$ group or a boronic acid pinacol ester group.

To obtain compound VII rac-VII

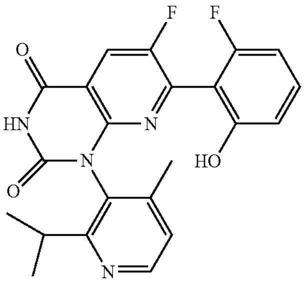

b) Mixing compound rac-VII with suitable salts and solvents or solvents to obtain M-VII in a form of a salt, cocrystal, solvate or any other polymorph mixture.

c) Optionally Neutralizing this M-VII salt or cocrystal to obtain the M-VII base.

M-VII

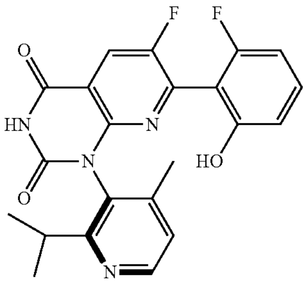

d) Reacting compound M-VII base with the compound IX

IX

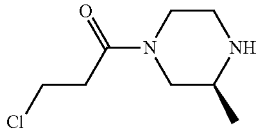

to obtain compound X:

X

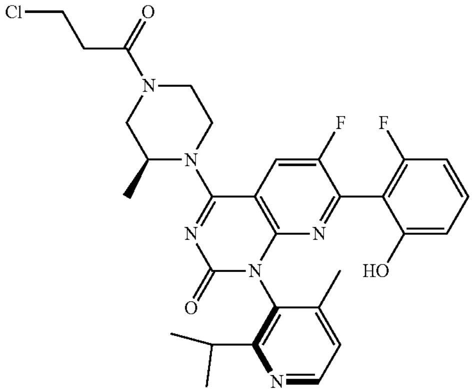

e) Reacting compound X in conditions of basic eliminations to give compound I:

I

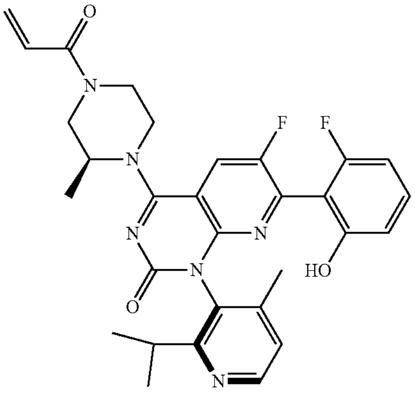

f) Alternatively, to step d) and e) reacting compound M-VII base with the compound XI

XI

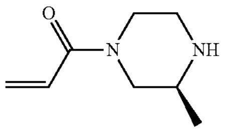

to obtain compound I.

Alternatively, the present disclosure provides a process for preparation of Sotorasib and salts thereof via a route to atropoisomer separation of compound rac-X. Said process comprising:

g) Reacting compound of formula VII

*rac*-VII

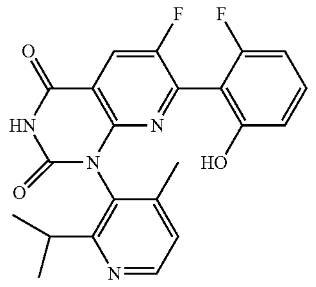

with the compound of formula IX

IX

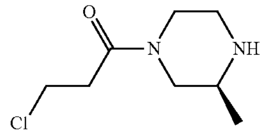

To obtain compound X

*rac*-X

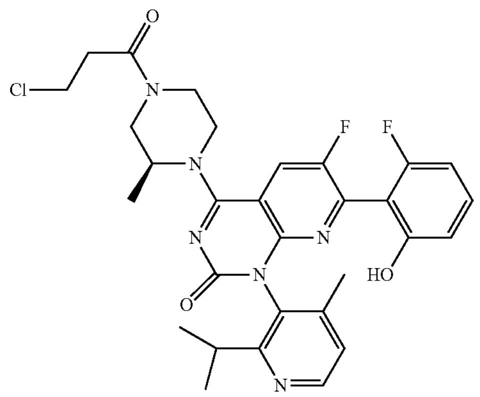

h) Mixing of compound rac-X with suitable salts and solvents or solvents to obtain X in a form of a salt, cocrystal, solvate or any other polymorph mixture.

i) Optionally Neutralizing this X salt or cocrystal to obtain the X base.

X

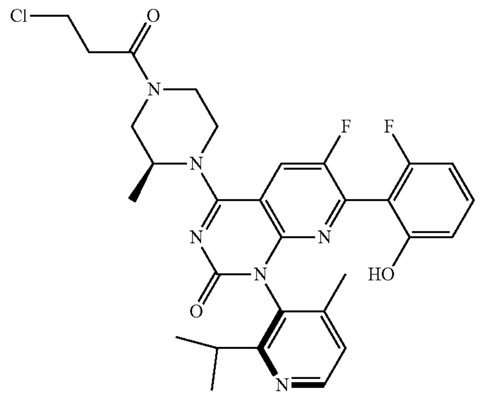

j) Reacting compound X in conditions of basic eliminations to give compound I.

In other embodiments the present disclosure provides intermediates for the preparation of compound I.

The present disclosure further comprises a process for the preparation of Sotorasib (Compound I), comprising reacting compound X:

X

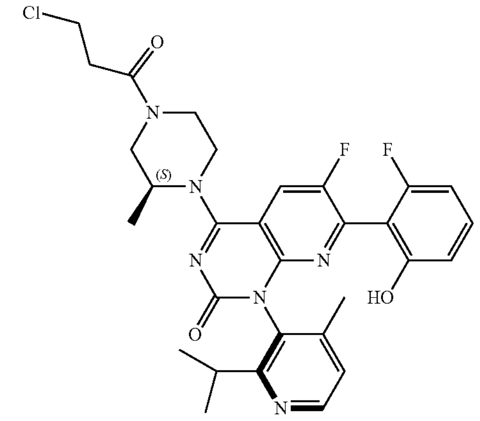

in conditions of basic elimination. Accordingly, there is provided a process for preparing Sotorasib comprising β-elimination reaction of the compound of formula X:

X

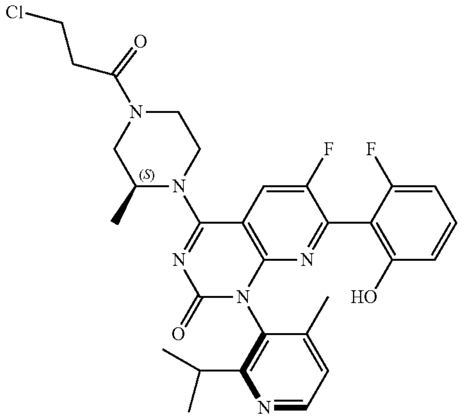

The reaction is carried out using a base. The base may be an inorganic base, particularly selected from an alkali metal hydroxide, an alkali metal carbonate, or an alkali metal phosphate. The reaction is preferably conducted in a polar solvent or a mixture of polar solvents.

According to any aspect of embodiment of the disclosed processes, suitable bases for the elimination reaction include: an alkali metal hydroxide, optionally wherein the base is sodium hydroxide or potassium hydroxide; an alkali metal carbonate, optionally selected from a potassium carbonate, sodium carbonate, cesium carbonate; or an alkali metal phosphate, optionally selected from potassium phosphate and sodium phosphate. Particularly preferred bases are alkali metal hydroxides, optionally sodium hydroxide or potassium hydroxide, and particularly potassium hydroxide.

According to any aspect of embodiment of the disclosed processes, the elimination reaction is preferably conducted in a polar solvent. Particularly, the polar solvent may comprise acetonitrile or a protic solvent, or mixtures thereof. Preferably, the protic solvent comprises water. More preferably, the polar solvent is a mixture of acetonitrile and water.

According to any aspect of embodiment of the disclosed processes, the reaction may be conveniently conducted at about ambient temperature. Preferably the reaction is carried out at a temperature of: about 20° C. to about 30° C., about 22° C. to about 27° C., or about 25° C.

According to any aspect of embodiment of the disclosed processes, the Sotorasib may be isolated from the reaction mixture in any form, preferably a solid form, and more preferably a crystalline form.

According to any aspect of embodiment of the disclosed processes, the reaction mixture may be quenched with a mineral acid, optionally selected from hydrochloric acid, sulfuric acid or phosphoric, preferably with a mineral acid, particularly phosphoric acid. Preferably, sufficient acid is added to adjust the pH to about 5.8 to about 7.2, about 6.0 to about 7.0, about 6.4 to about 6.8, or about 6.6. Optionally, a $C_{1-3}$ alcohol is added to the reaction mixture before or after quenching with the mineral acid. Preferably, the $C_{1-3}$ alcohol is methanol.

According to any aspect of embodiment of the disclosed processes, Sotorasib may be isolated. Preferably Sotorasib is isolated from the reaction mixture by a process comprising:

(a) heating the quenched reaction mixture, optionally to a temperature of: about 35° C. to about 70° C., about 40° C. to about 55° C., or about 45° C.;

(b) optionally adjusting the pH of the mixture to: about 5.8 to about 7.2, about 6.0 to about 7.0, about 6.4 to about 6.8, or about 6.6 and optionally adding water, to form a solution;

(c) optionally adding seed crystals of Sotorasib, preferably where the seed crystals are Sotorasib Form H5, as described in any aspect or embodiment of the disclosure;

(d) stirring the mixture at a temperature of: about 35° C. to about 70° C., about 40° C. to about 55° C., or about 45° C., preferably for about 10 minutes to about 5 hours, about 20 minutes to about 4 hours, about 30 minutes to about 2 hours, or about 1 hour;

(e) cooling the mixture, optionally to a temperature of: about 20° C. to about 30° C., or about 22° C. to about 27° C., or about 25° C.;

(f) optionally adding water;

(g) optionally stirring the mixture for about 30 minutes to about 10 hours;

(h) optionally cooling the mixture, preferably to a temperature of: about −10° C. to about 15° C., about −5° C. to about 10° C., about −2° C. to about 8° C., or about 0° C. to about 5° C.;

(i) optionally stirring the cooled mixture for about 20 minutes to about 5 hours, about 40 minutes to about 4 hours, or about 50 minutes to about 2 hours; and (j) optionally isolating Sotorasib by filtration, decantation or centrifuge.

According to any aspect of embodiment of the disclosed processes, the Sotorasib may be isolated by filtration. The Sotorasib may be dried, optionally at a temperature of: about 40° C. to about 90° C., about 50° C. to about 80° C., about 65° C. to about 75° C., or about 70° C., preferably wherein the drying is at reduced pressure.

Advantageously, the processes as described in any aspect of embodiment of the disclosure may be used to obtain crystalline Sotorasib directly from the reaction mixture, for example without the need for a separate crystallisation step from an isolated crude product. Particularly according to any aspect of embodiment of the disclosed processes, Sotorasib crystalline Form H5 as described in any aspect or embodiment herein may be obtained in high purity, directly (e.g. without first isolating a crude Sotorasib, and subjecting the crude product to a separate crystallisation step) from the reaction process.

According to any aspect of embodiment of the disclosed processes, there is provided a process for preparing compound X, wherein the process comprises reacting the compound XV:

XV

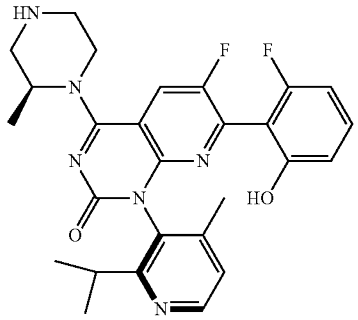

with 3-chloropropionyl chloride (Compound XVII), preferably in the presence of a base and a solvent. Preferably, the process is carried out in the presence of a base. The reaction may be carried out in a solvent, preferably polar aprotic solvent, and more preferably a chlorinated hydrocarbon, such as dichloromethane or lactam such as NMP. The base may be any suitable organic or inorganic base, preferably an organic base, such as a mono, di, or trialkylamine, preferably a mono-, di-, or tri($C_{1-6}$)alkylamine, or a mono-, di-, or tri($C_{1-3}$) alkylamine, wherein the alkyl groups in the di- or trialkylamine may be the same or different. A particularly suitable base is N,N-diisopropylethylamine. The process preferably comprises preparing a reaction mixture comprising compound XV, a base, and 3-chloropropionyl chloride, in the solvent. Preferably the reaction mixture is prepared by combining compound XV with the base, and adding 3-chloropropionyl chloride, optionally wherein the addition is in portions or dropwise. The reaction may be stirred at about room temperature. The mixture may be stirred for a suitable time, such as: about 15 minutes to about 10 hours, about 20 minutes to about 9 hours or about 30 minutes to about 8 hours. The reaction mixture may be quenched with an inorganic base, such as an alkali metal carbonate, or an alkali metal hydrogen carbonate, preferably sodium carbonate, sodium bicarbonate, potassium carbonate or potassium hydrogen carbonate, and particularly sodium carbonate or potassium carbonate, and most particularly potassium carbonate. Preferably the compound X is isolated by crystallisation from the reaction mixture. Advantageously, the compound X may be isolated directly as crystals from the reaction mixture after quenching (i.e. without requiring separate purification of an isolated crude product. Moreover, the compound X may be isolated directly as crystals from the reaction mixture after quenching in high yield and high purity. The present disclosure further provides a process for Sotorasib, comprising preparing compound X as described in any aspect or embodiment of the disclosure, and converting the compound X to Sotorasib. The conversion of compound X to Sotorasib may be carried out by beta-elimination of compound X as described in any aspect or embodiment of the present disclosure According to any aspect or embodiment of the disclosed processes, the compound XV may be prepared by deprotection of a compound of formula XIV:

XIV

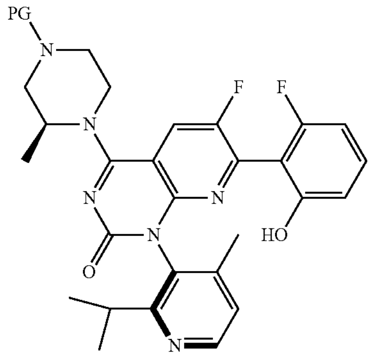

wherein PG is a protecting group, preferably wherein PG is an acid-labile protecting group. Acid-labile protecting groups are well known, and tert-butyloxycarbonyl (tBOC) is a particularly preferred protecting group. According to any aspect or embodiment of the disclosed processes, the compound XIV may be prepared by reaction of Compound XIII:

XIII

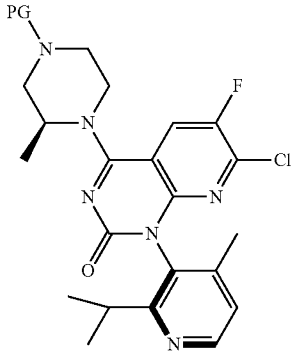

with the compound VIII:

VIII

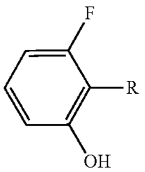

wherein R is $B(OH)_2$ or a boronic acid pinacol ester, for example, under Suzuki coupling conditions.

According to any aspect or embodiment of the disclosed processes, there is provided a process for preparing compound XIII by chiral purification of a diastereomeric mixture of compound XIII. In particular, the process for preparing compound XIII by crystallization from a diastereomeric mixture of compound XIII:

XIII

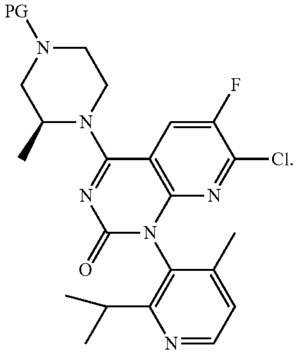

According to any aspect or embodiment of the present disclosure, the crystallization may be carried out using a suitable solvent. Particularly suitable solvents include alcohols, preferably aliphatic alcohols (especially $C_{1-6}$ alcohols, or $C_{1-3}$ alcohols, and more especially ethanol, n-propanol, isopropanol, or butanol), ketones (especially $C_{3-6}$ ketones, more especially acetone, methylethylketone, or methylisobutylketone, and particularly acetone or methylisobutylketone), esters (particularly $C_{3-6}$ esters, and more particularly methylacetate, ethylacetate or isobutylacetate), a nitrile (preferably acetonitrile), aromatic hydrocarbons (particularly $C_{6-10}$ aromatic hydrocarbons, and preferably toluene), and water, or a combination thereof. Preferably, the crystallisation is carried out in ethanol, n-butanol, isopropanol, butanol, acetone, methylisobutylketone, methylacetate, ethylacetate, isobutyl acetate or toluene, and most preferably acetone, ethanol, methylacetate, ethylacetate, or isopropanol. Preferably, the process comprises crystallising Compound XIII from a the diastereomeric mixture of compound XIII in the above-described solvents. Preferably the process comprises heating the solution, optionally to a temperature of: about 40° C. to about 90° C., about 50° C. to about 80° C., about 55° C. to about 70° C., or about 60° C., and cooling to crystallise compound XIII. The mixture may be cooled to: about −5° C. to about 30° C., about −2° C. to about 25° C., or about 0° C. to about 25° C. Optionally seed crystals of compound VIII may be added. The mixture may be stirred for a suitable time, such as: about 2 hours to about 48 hours, about 6 hours to about 36 hours, about 10 hours to about 28 hours, about 18 to about 24 hours, or about 22 hours.

According to a further aspect of the present invention, there is provided a process for preparing compound X comprising preparing compound XIII by crystallisation from a diastereomeric mixture of compound XIII, converting the compound XIII to compound XV (preferably by reacting compound XIII with VIII to form XIV, optionally under Suzuki conditions), and deprotecting), and reacting compound XV with compound XVII. According to another aspect of the present invention, there is provided a process for preparing Sotorasib comprising preparing compound XIII by crystallisation from a diastereomeric mixture of compound XIII, converting the compound XIII to compound XV (preferably by reacting compound XIII with VIII to form XIV, optionally under Suzuki conditions, and deprotecting), and reacting compound XV with compound XVII to obtain compound X, and converting compound X to Sotorasib. Preferably the conversion of compound X to Sotorasib is carried out by beta-elimination of compound X with a base selected from an inorganic base, particularly an alkali metal hydroxide, an alkali metal carbonate, or an alkali metal phosphate, preferably wherein the reaction is conducted in a polar solvent or a mixture of polar solvents. The beta-elimination reaction of compound X to form Sotorasib may be carried out according to any of the herein described aspects and embodiments.

According to any aspect or embodiment of the disclosed processes, diastereoisomeric mixture of compound XIII may be prepared by reaction of rac-XII:

rac-XII

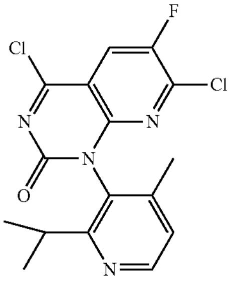

with the compound XVI:

XVI

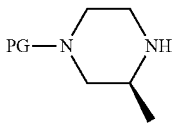

optionally in the presence of a base and a solvent.

According to any aspect or embodiment of the disclosed processes, the compound rac-XII may be prepared by chlorination of a compound rac-VI:

rac-VI

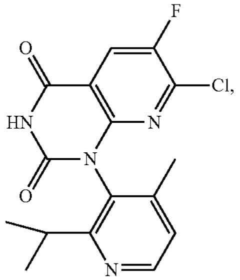

with any suitable chlorinating agent, preferably with $POCl_3$ or $PCl_5$.

Embodiments of the disclosed process may be represented in the Scheme IV:

Scheme IV

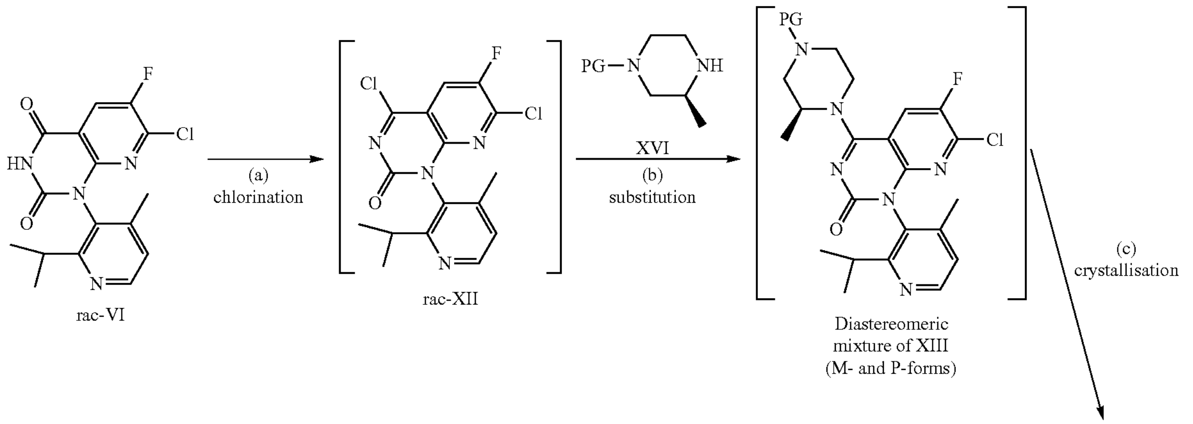

-continued

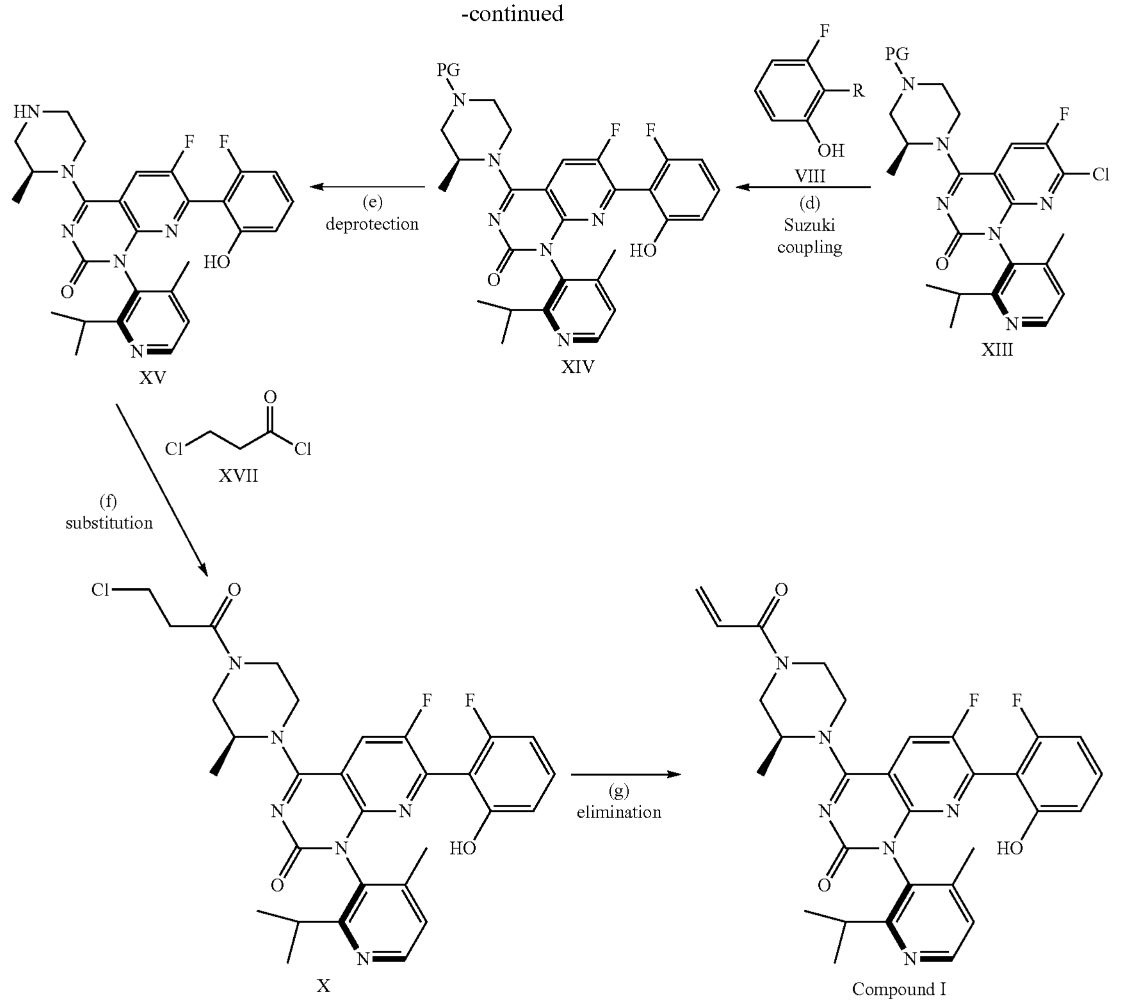

In Scheme IV, PG represents any suitable protecting group for the piperidyl nitrogen. Suitably, PG represents an acid labile protecting group. These are well known to the skilled person. Tert-butyloxycarbonyl is a particularly suitable protecting group. Accordingly, it is preferred that PG in the intermediates XIII and XIV is t-butyloxycarbonyl. In Scheme IV, the group R in compound VIII is preferably a borate, such as $B(OH)_2$ or a bis-pinacolate (Bpin), and preferably $B(OH)_2$. Compounds rac-VII and XIII need not be isolated from the reaction mixture.

A key intermediate in the synthesis of Sotorasib (Compound I) is compound X; Compound X can be readily converted to Sotorasib by base-mediated beta-elimination as described in any embodiment or aspect of the present disclosure. The process of the present disclosure whereby Sotorasib is prepared by an elimination reaction of compound X [i.e. step (g)] enables the preparation of Sotorasib without the need to use acryloylchloride, which is a dangerous and highly toxic substance, and which is therefore undesirable for use in large scale preparations. Advantageously the present process of preparing Sotorasib from compound X enables the production of Sotorasib in high yield and high purity. Surprisingly, Sotorasib can be isolated as a crystalline material directly from the reaction, particularly without the need to first isolate the product as a crude solid. The compound X can be made by reaction of compound XV with 3-chloropropionyl chloride (XVII) as described in step (f) in Scheme IV.

The disclosure further provides the following aspects:

- the preparation of Sotorasib (optionally in crystalline form H5) starting from Compound X by step (g);
- the preparation of compound X starting from Compound XV by reaction with XVII according to step (f), and optionally converting the compound X to Sotorasib (preferably by step (g), and preferably wherein the Sotorasib is crystalline form H5);
- the preparation of compound X starting from compound rac-VI by steps (a), (b), (c), (d), (e), and (f) as indicated in Scheme IV, and optionally converting the compound X to Sotorasib (preferably by step (g);
- the preparation of Sotorasib (Compound I, optionally in crystalline form H5) starting from compound rac-VI by steps (a), (b), (c), (d), (e), (f) and (g) as indicated in Scheme IV.

According to any aspect or embodiment of the disclosure, Sotorasib may preferably be in the form of the (M)-atropisomer. In particular, Sotorasib may be atropisomerically pure and is substantially free of the (P)-atropisomer of the compound. Preferably, Sotorasib contains: about 0.5% (w/w) or less, about 0.4% (w/w) or less, about 0.3% (w/w) or less, about 0.2% (w/w) or less, about 0.1% (w/w) or less, about 0.05 (w/w) or less, about 0.02 (w/w) or less, or about 0%, of the (P)-atropisomer of the compound.

According to any aspect or embodiment of the disclosed processes, any of the processes described herein for preparing Sotorasib further comprises combining the Sotorasib or a salt thereof with at least one pharmaceutically acceptable excipient to prepare a pharmaceutical composition.

In further embodiment the present disclosure provides a compound of formula VII:

VII

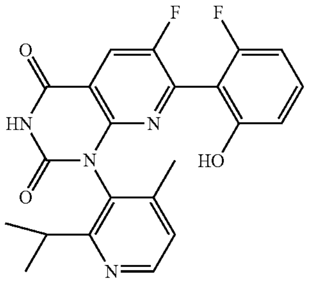

Compound formula VII has the chemical name 6-fluoro-7-(2-fluoro-6-hydroxyphenyl)-1-(2-isopropyl-4-methylpyridin-3-yl)pyrido[2,3-d]pyrimidine-2,4(1H,3H)-dione and may optionally be in the form of a salt, solvate or cocrystal, optionally wherein the compound, or a salt, solvate or cocrystal thereof, may be in the form of: a mixture of atropisomers, or isolated M-atropisomer. The Compound VII, or a salt, solvate or cocrystal thereof, optionally in the form of a mixture of atropisomers, or isolated M atropisomer may be advantageously used in the preparation of Sotorasib, or may be used as reference standards for intermediates in the process.

The present disclosure further provides a compound of formula:

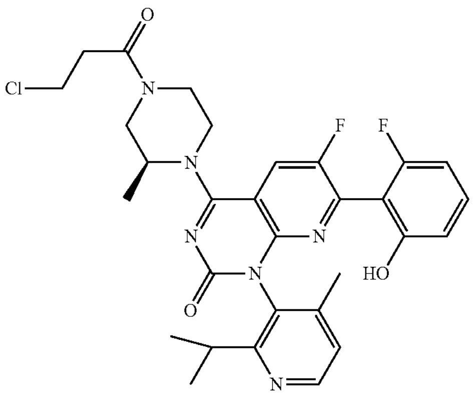 [SMILES: Cc1ccnc(C(C)C)c1-n1c(=O)nc(N2CCN(C(=O)CCCl)C[C@@H]2C)c2cc(F)c(-c3c(O)cccc3F)nc21]

This compound has the chemical name 4-((S)-4-(3-chloropropanoyl)-2-methylpiperazin-1-yl)-6-fluoro-7-(2-fluoro-6-hydroxyphenyl)-1-(2-isopropyl-4-methylpyridin-3-yl)pyrido[2,3-d]pyrimidin-2(1H)-one, and may be in form of a base, mixture of atropomers, isolated M- or P-atropomers or their salts, solvates or cocrystals, which may be advantageously used in the preparation of Sotorasib. Thus, the compound or a salt, solvate or cocrystal thereof, optionally in the form of a mixture of atropisomers, or isolated M- and P-atropisomers may be advantageously used in the preparation of Sotorasib, or may be used as reference standards, e.g. for determining the purity of the intermediates and final product in the process. It will be appreciated that the above compound, in the form of the M-atropisomer, corresponds to Compound X. It will further be appreciated that the above compound may be prepared as a mixture of atropisomers by omitting the crystallisation step (c) as depicted in Scheme IV. The above compound, in the form of the P-atropisomer, may be isolated from the crystallisation step (c), for example, from the crystallisation mother liquor.

In a further embodiment, the present disclosure provides the compound M-VII depicted below:

M-VII

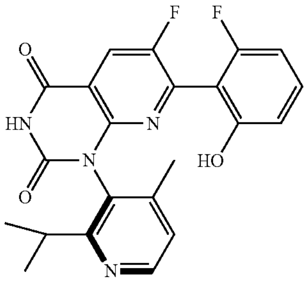

The compound formula M-VII having the chemical name 6-fluoro-7-(2-fluoro-6-hydroxyphenyl)-1-(2-isopropyl-4-methylpyridin-3-yl)pyrido[2,3-d]pyrimidine-2,4(1H,3H)-dione, may be in form of a base, salt, solvate or cocrystal.

The present disclosure further provides the compound X:

X

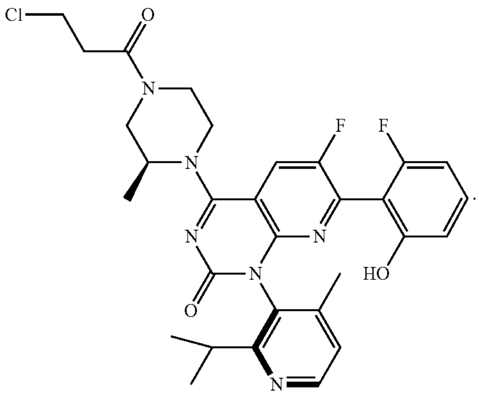

The compound formula X having the chemical name 4-((S)-4-(3-chloropropanoyl)-2-methylpiperazin-1-yl)-6-fluoro-7-(2-fluoro-6-hydroxyphenyl)-1-(2-isopropyl-4-methylpyridin-3-yl)pyrido[2,3-d]pyrimidin-2(1H)-one may be in form of a base, salt, solvate or cocrystal.

The process depicted below in Scheme V is an alternative specific embodiment of the present disclosure Scheme V
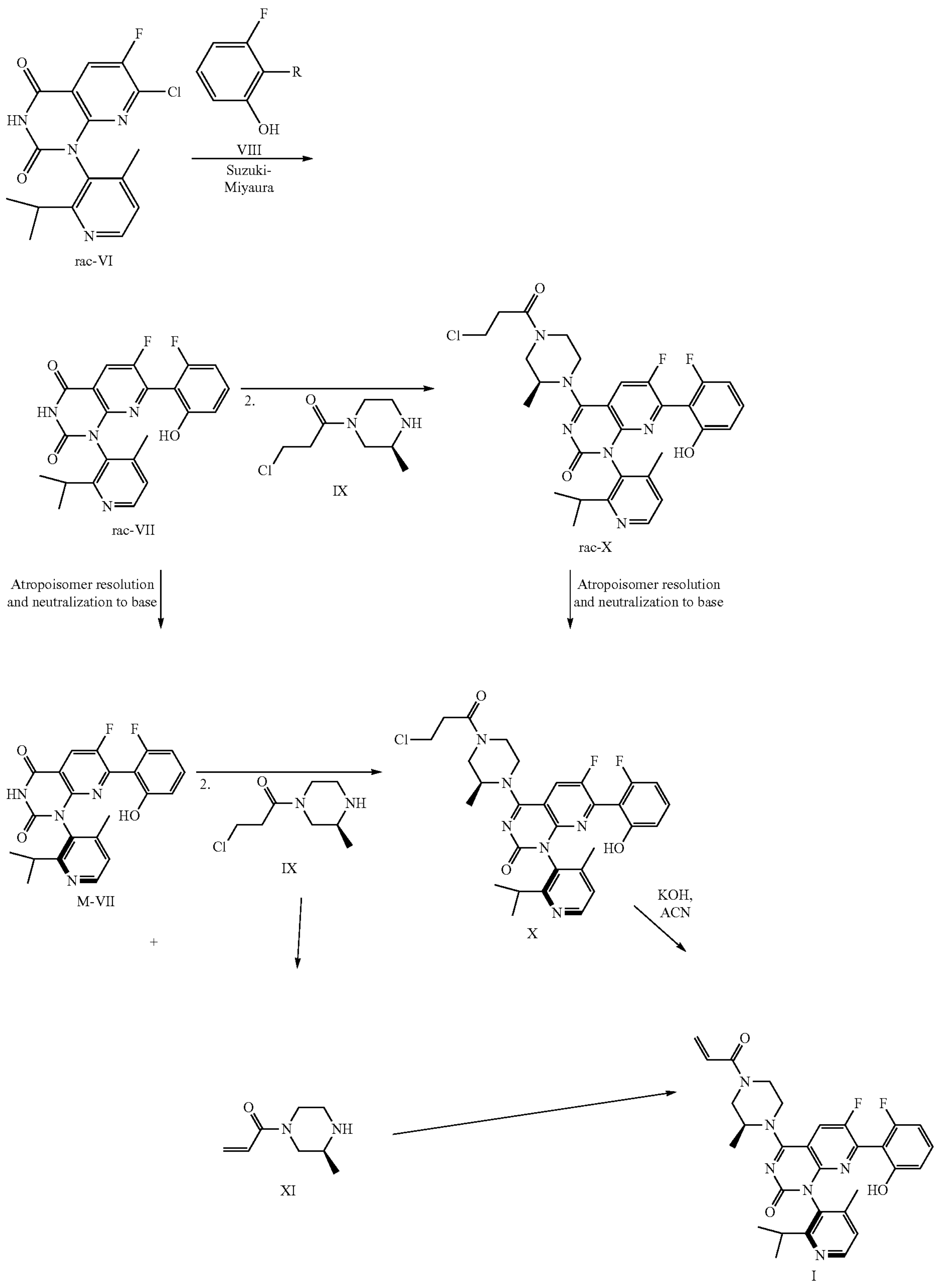

In another aspect the present disclosure provides the use of any one of the intermediates described herein (and particularly compound X) for the preparation of Sotorasib and salts thereof.

In another aspect the disclosure provides Sotorasib and salts thereof produced by the processes of the present disclosure.

Sotorasib or Sotorasib salt produced by the process of the present disclosure may be used in the preparation of pharmaceutical compositions of Sotorasib or Sotorasib salts.

The present disclosure also provides methods of treatment of NSCLC, comprising administrating a therapeutically effective amount of Sotorasib or salts thereof prepared by the process of the present disclosure, to a subject in need of the treatment. In embodiments, Sotorasib or salts thereof prepared by the process of the present disclosure and the pharmaceutical compositions and/or formulations of the present disclosure may be used in the treatment of KRAS G12C-mutant tumors; particularly KRAS G12C-mutant solid tumors; particularly non-small-cell lung cancer, colorectal cancer, pancreatic cancer, appendiceal cancer, endometrial cancer, and melanoma; more particularly in the treatment of non-small-cell lung cancer or colorectal cancer; or in the treatment of advanced or metastatic non-small-cell lung cancer or colorectal cancer, and more particularly locally advanced or metastatic non-small-cell lung cancer or colorectal cancer, and especially in the treatment of advanced or metastatic non-small-cell lung cancer or colorectal cancer following at least one prior systemic therapy.

In another aspect of the disclosure, the present disclosure encompasses solid state forms of Sotorasib, including crystalline polymorphs of Sotorasib, crystalline polymorphs of Sotorasib salts, cocrystals of Sotorasib, processes for preparation thereof, and pharmaceutical compositions thereof.

Solid state properties of Sotorasib and crystalline polymorphs thereof can be influenced by controlling the conditions under which Sotorasib and crystalline polymorphs thereof are obtained in solid form.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, a crystalline polymorph of Sotorasib described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject crystalline polymorph of Sotorasib. In some embodiments of the disclosure, the described crystalline polymorph of Sotorasib may contain from about 1% to about 20% (w/w), from about 5% to about 20% (w/w), or from about 5% to about 10% (w/w) of one or more other crystalline polymorph of the same Sotorasib.

Depending on which other crystalline polymorphs a comparison is made, the crystalline polymorphs of Sotorasib of the present disclosure may have advantageous properties selected from at least one of the following: chemical purity, flowability, solubility, dissolution rate, morphology or crystal habit, stability, such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility and bulk density.

A solid state form, such as a crystal form or an amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Sotorasib referred to herein as being characterized by graphical data "as depicted in" or "as substantially depicted in" a Figure will thus be understood to include any crystal forms of Sotorasib characterized with the graphical data having such small variations, as are well known to the skilled person, in comparison with the Figure.

As used herein, and unless stated otherwise, the term "anhydrous" in relation to crystalline forms of Sotorasib, relates to a crystalline form of Sotorasib which does not include any crystalline water (or other solvents) in a defined, stoichiometric amount within the crystal. Moreover, unless otherwise indicated, an "anhydrous" form would generally not contain more than 1% (w/w), of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, the term "isolated" in reference to crystalline polymorph of Sotorasib of the present disclosure corresponds to a crystalline polymorph of Sotorasib that is physically separated from the reaction mixture in which it is formed.

As used herein, unless stated otherwise, the XRPD measurements are taken using copper K$\alpha$ radiation wavelength 1.54184 Å. XRPD peaks reported herein are measured using CuK $\alpha$ radiation, $\lambda$=1.54184 Å, typically at a temperature of 25±3° C.

As used herein, unless stated otherwise, solid state $^{13}C$ NMR spectra are measured 700 MHz at a magic angle spinning frequency r/2=18 kHz, preferably room temperature.

As used herein, unless stated otherwise, solid state $^{19}F$ NMR spectra are measured 700 MHz at a magic angle spinning frequency r/2=22 kHz, preferably at room temperature.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, in some cases about 16 hours.

As used herein, the term "reduced pressure" refers to a pressure that is less than atmospheric pressure. For example, reduced pressure is about 10 mbar to about 50 mbar.

As used herein and unless indicated otherwise, the term "ambient conditions" refer to atmospheric pressure and a temperature of 22-24° C.

The present disclosure provides a crystalline polymorph of Sotorasib, designated Form H5. The crystalline Form H5 of Sotorasib may be characterized by data selected from one or more of the following: an X-ray powder diffraction pattern substantially as depicted in FIG. 1; an X-ray powder diffraction pattern having peaks at 4.4, 5.3 and 7.6 degrees 2-theta±0.2 degrees 2-theta; and combinations of these data. Crystalline Form H5 of Sotorasib may be further characterized by an X-ray powder diffraction pattern having peaks at 4.4, 5.3 and 7.6 degrees 2-theta±0.2 degrees 2-theta, and also having any one, two, three, four, five, six or seven additional peaks selected from 6.4, 10.7, 16.4, 18.0, 19.0, 19.5 and 21.3 degrees 2-theta±0.2 degrees 2-theta.

Crystalline Form H5 of Sotorasib may be alternatively characterized by data selected from one or more of the following: an X-ray powder diffraction pattern substantially as depicted in FIG. 1; an X-ray powder diffraction pattern having peaks at 4.4, 5.3, 6.4, 7.6 and 19.5 degrees 2-theta±0.2 degrees 2-theta; and combinations of these data. Crystalline Form H5 of Sotorasib may be further characterized by an X-ray powder diffraction pattern having peaks at 4.4, 5.3, 6.4, 7.6 and 19.5 degrees 2-theta±0.2 degrees 2-theta, and also having any one, two, three, four, or five additional peaks selected from 10.7, 16.4, 18.0, 19.0 and 21.3 degrees 2-theta±0.2 degrees 2-theta.

Crystalline Form H5 of Sotorasib may be alternatively characterized by an X-ray powder diffraction pattern having peaks at 4.4, 5.3, 6.4, 7.6, 10.7, 16.4, 18.0, 19.0, 19.5 and 21.3 degrees 2-theta±0.2 degrees 2-theta.

Crystalline Form H5 of Sotorasib may be a characterized by a solid state $^{13}C$ NMR spectrum having signals at about 11.4, 15.2, 22.1, 106.1 and 166.6±0.2 ppm. Crystalline Form H5 of Sotorasib may be further characterized by a solid state $^{13}C$ NMR spectrum having the following chemical shift absolute differences from a peak at 47.0 ppm±1 ppm of: 35.6, 31.8, 24.9, 59.1 and 119.6 ppm±0.1 ppm. Alternatively crystalline Form H5 of Sotorasib may be a characterized by the solid state $^{13}C$ NMR data in combination with the characteristic XRPD peaks as described in any of the aspects and embodiments disclosed herein.

Crystalline Form H5 of Sotorasib may be a characterized by $^{19}F$ NMR spectrum having signals at about −114.1, −119.9, −126.7 and −131.8±0.2 ppm. Alternatively crystalline Form H5 of Sotorasib may be a characterized by the $^{19}F$ NMR spectrum in combination with the characteristic XRPD peaks or solid state $^{13}C$ NMR spectrum as described in any of the aspects and embodiments disclosed herein.

Crystalline Form H5 of Sotorasib may alternatively be characterized by unit cell parameters (293 K)

| Unit cell parameter | Form H5 |
|---|---|
| cell_length_a | 7.304(1) Å |
| cell_length_b | 25.032(3) Å |
| cell_length_c | 33.233(3) Å |
| cell_angle_alpha | 90° |
| cell_angle_beta | 90° |
| cell_angle_gamma | 90° |
| cell_volume | 6076(1) $Å^3$ |
| symmetry_cell_setting | Orthorhombic |
| Symmetry space group name | P $2_12_12_1$ |

Alternatively crystalline Form H5 of Sotorasib may be a characterized by the unit cell parameters in combination with the characteristic XRPD peaks, solid state $^{13}C$ NMR spectrum or $^{19}F$ NMR spectrum as described in any of the aspects and embodiments disclosed herein.

In one embodiment of the present disclosure, crystalline Form H5 of Sotorasib is isolated.

Crystalline Form H5 of Sotorasib may be a hydrate form. Optionally Form H5 may contain: about 1 to about 8 wt %, about 2 to about 7.5 wt %, about 3 to about 7 wt %, about 3.5 to about 6.5 wt %, about 3.5 to about 6.2 wt % or about 3.6 to about 6.1 wt %, of water.

Crystalline Form H5 of Sotorasib may be characterized by each of the above characteristics alone or by all possible combinations, e.g., an XRPD pattern having peaks at 4.4, 5.3 and 7.6 degrees 2-theta±0.2 degrees 2-theta; an XRPD pattern as depicted in FIG. 1, and combinations thereof.

Crystalline Form H5 of Sotorasib, according to any aspect or embodiment described herein may be polymorphically pure or may be substantially free of any other solid state forms of the subject Sotorasib. In any aspect or embodiment of the present disclosure, the crystalline form H5 may contain: no more than about 20% (w/w), no more than about 10% (w/w), no more than about 5% (w/w), no more than about 2% (w/w), no more than about 1% (w/w), or about 0% (w/w) of any other solid state forms of Sotorasib.

Crystalline Form H5 according to any aspect or embodiment of the present disclosure may contain: no more than about 20%, no more than about 10%, no more than about 5%, no more than about 2%, no more than about 1% or about 0% of amorphous Sotorasib.

Crystalline Form H5 according to any aspect or embodiment of the present disclosure may be atropisomerically pure.

Crystalline Form H5 according to any aspect or embodiment of the present disclosure may be (M)-Sotorasib.

Crystalline Form H5 according to any aspect or embodiment of the present disclosure may be atropisomerically pure and may be substantially free of (P)-Sotorasib. Particularly, crystalline form H5 according to any aspect or embodiment of the present disclosure may be (M)-Sotorasib containing: about 0.5% (w/w) or less, about 0.4% (w/w) or less, about 0.3% (w/w) or less, about 0.2% (w/w) or less, about 0.1% (w/w) or less, about 0.05 (w/w) or less, about 0.02 (w/w) or less, or about 0%, of (P)-Sotorasib.

The present disclosure further provides a process comprising combining the crystalline form of Sotorasib as described in any aspect or embodiment of the present disclosure with at least one pharmaceutically acceptable excipient to prepare a pharmaceutical composition or pharmaceutical formulation.

The present disclosure provides crystalline forms of Sotorasib, or a pharmaceutical composition or pharmaceutical composition which is obtainable by the processes described in any of the embodiments described above and herein.

The present disclosure provides a process for preparing other solid state forms of Sotorasib, Sotorasib salts and their solid state forms thereof. The process includes preparing any one of the solid state forms of Sotorasib by the processes of the present disclosure, and converting it to other Sotorasib salt(s).

The present disclosure provides the above described solid state forms of Sotorasib for use in the preparation of pharmaceutical compositions comprising Sotorasib and/or crystalline polymorphs thereof.

The present disclosure also provides the use of solid state forms of Sotorasib of the present disclosure for the preparation of pharmaceutical compositions of Sotorasib and/or crystalline polymorphs thereof. In particular the present disclosure provides the above described solid state forms of Sotorasib and salts thereof, for the preparation of a pharmaceutical composition or formulation, preferably an oral formulation in the form of a solid dispersion comprising Sotorasib or salt thereof.

The present disclosure provides processes for preparing the above mentioned pharmaceutical compositions. The processes include combining any one or a combination of the solid state forms of Sotorasib of the present disclosure with at least one pharmaceutically acceptable excipient.

The present disclosure further provides pharmaceutical compositions comprising the solid state forms of Sotorasib and salts thereof, or combinations thereof, according to the present disclosure.

Pharmaceutical combinations or formulations of the present disclosure contain any one or a combination of the solid state forms of Sotorasib of the present disclosure. In addition to the active ingredient, the pharmaceutical formulations of the present disclosure can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present disclosure include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, Sotorasib and any other solid excipients can be dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, xanthan gum and combinations thereof.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the route of administration is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, such as a powdered or granulated solid composition of the disclosure, within either a hard or soft shell. The shell can be made from gelatin and optionally contain a plasticizer such as glycerin and/or sorbitol, an opacifying agent and/or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present disclosure can include any of the aforementioned blends and granulates that were described with reference to tableting, but they are not subjected to a final tableting step.

A pharmaceutical formulation of Sotorasib can be administered. Sotorasib may be formulated for administration to a mammal, in embodiments to a human, by injection. Sotorasib can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The solid state forms of Sotorasib and the pharmaceutical compositions and/or formulations of Sotorasib of the present disclosure can be used as medicaments, in embodiments in the treatment of cancer, in particular non-small cell lung cancer and/or colorectal cancers. In embodiments, the solid state forms of Sotorasib and the pharmaceutical compositions and/or formulations of the present disclosure may be used in the treatment of KRAS G12C-mutant tumours; particularly KRAS G12C-mutant solid tumours; particularly non-small-cell lung cancer, colorectal cancer, pancreatic cancer, appendiceal cancer, endometrial cancer, and melanoma; more particularly in the treatment of non-small-cell lung cancer or colorectal cancer; or in the treatment of advanced or metastatic non-small-cell lung cancer or colorectal cancer, and more particularly locally advanced or metastatic non-small-cell lung cancer or colorectal cancer, and especially in the treatment of advanced or metastatic non-small-cell lung cancer or colorectal cancer following at least one prior systemic therapy.

The present disclosure also provides methods of treating cancer, in particular non-small cell lung and/or colorectal cancers, by administering a therapeutically effective amount of any one or a combination of the solid state forms of Sotorasib of the present disclosure, or at least one of the above pharmaceutical compositions and/or formulations, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

Powder X-Ray Diffraction ("XRPD") Method

Sample after being powdered in a mortar and pestle is applied directly on a silicon plate holder. The X-ray powder diffraction pattern was measured with Philips X'Pert PRO X-ray powder diffractometer, equipped with Cu irradiation source=1.54184 Å (Ångström), X'Celerator (2.022° 2θ) detector. Scanning parameters: angle range: 3-40 deg., step size 0.0167, time per step 37 s, continuous scan. Peak positions were determined without using silicon powder as an internal standard.

Solid-State NMR Methods

Typically, the solid-state NMR spectra are measured at 11.7 T using a Bruker Avance III HD 500 US/WB NMR spectrometer (Karlsruhe, Germany, 2013) with a 4- or 3.2-mm probehead.

For the correct measurements of all the spectra, the recycle delay D1 is optimized experimentally by the measurement of $^{1}H$ MAS NMR spectra with variable repetition delay. In this optimization the $^{1}H$ MAS NMR spectra are recorded with dummy scans, the number of which is DS=8 and number of scans NS=1. The D1 delay is gradually (step-by-step) increased from the initial value D1=0.5 s by multiplying using the factor n=2. This way, the build-up of intensity of $^{1}H$ NMR signals is monitored. The whole procedure is finished when the constant (equilibrium) signal intensity is reached. The repetition delay D1 used for the measurement of CP/MAS NMR spectra is then set to be 80% of the obtained equilibrium value. $^{1}H$ MAS NMR spectra are measured at MAS frequency of 15 kHz using a single-pulse experiment with the number of scans 32.

Frictional heating of the spinning samples is compensated by active cooling, and the temperature calibration is performed with $Pb(NO_3)_2$.

The NMR spectrometer is always completely calibrated and all experimental parameters are carefully optimized prior the recording of the spectra. Magic angle is set using KBr during the standard optimization procedure and homogeneity of magnetic field is optimized using adamantane sample (resulting line-width at half-height $Dn_{1/2}$ was less than 3.5 Hz at 250 ms of acquisition time).

Solid State $^{13}C$ NMR Method

Solid State $^{13}C$ NMR CP/MAS NMR spectra employing cross-polarization are acquired using the standard cross-polarization pulse scheme at spinning frequency of 18 kHz. The cross-polarization contact time is usually 2 ms, and the dipolar decoupling SPINAL64 is applied during the data acquisition. The number of scans is set for the signal-to-noise ratio SINO reaches at least the value ca. 50. The $^{13}C$ scale is referenced to a-glycine (176.03 ppm for $^{13}C$).

Solid State $^{19}F$ NMR Method

The $^{19}F$ MAS NMR spectra are measured at MAS frequency of 18 and 22 kHz using a single-pulse experiment with the number of scans ranging from 64 to 256 scans. The $^{19}F$ scale of chemical shifts is referenced to polytetrafluorethylene (PTFE) sample the central signal of which is set to −122 ppm. The spectra are usually recorded at two MAS frequencies, which allows distinguishing the central signals and spinning-side-bands (ssb). $^{19}F$ NMR chemical shift of central signals is independent of MAS frequency, whereas position of ssb's is MAS frequency dependent.

For the correct measurements of all the above-mentioned spectra, the recycle delay D1 is optimized experimentally by the measurement of $^{1}H$ MAS NMR spectra with variable repetition delay. In this optimization the $^{1}H$ MAS NMR spectra are recorded with dummy scans, the number of which is DS=8 and number of scans NS=1. The D1 delay is gradually (step-by-step) increased from the initial value D1=0.5 s by multiplying using the factor n=2. This way, the build-up of intensity of $^{1}H$ NMR signals is monitored. The whole procedure is finished when the constant (equilibrium) signal intensity is reached. The repetition delay D1 used for the measurement of CP/MAS NMR spectra is then set to be 80% of the obtained equilibrium value. Frictional heating of the spinning samples is compensated by active cooling, and the temperature calibration is performed with $Pb(NO_3)_2$.

The NMR spectrometer is always completely calibrated and all experimental parameters are carefully optimized prior the recording of the spectra. Magic angle is set using KBr during the standard optimization procedure and homogeneity of magnetic field is optimized using adamantane sample (resulting line-width at half-height $Dn_{1/2}$ was less than 3.5 Hz at 250 ms of acquisition time).

In some cases, the $^{13}C$, $^{15}N$ CP/MAS and $^{1}H$ MAS NMR spectra are alternatively recorded at 16.4 T using a Bruker Avance NEO 700 SB NMR spectrometer (Karlsruhe, Germany, 2021) with 3.2 mm probehead. In this case, the MAS frequency is set to 18-20 kHz for $^{13}C$ and $^{1}H$ NMR measurements, whereas $^{15}N$ CP/MAS NMR spectra are always measured at 10 kHz. All the other key experimental parameters are kept the same as used at 11.7 T for the Bruker 500 MHz spectrometer.

Indexation

Powder diffraction patterns of Sotorasib Form H5 was measured at laboratory temperature, and analysed by program Highscore. The correctness of indexation was supported by LeBail fit, and the unit cell volume calculation.

EXAMPLES

Preparation of Starting Materials

Sotorasib can be prepared according to methods known from the literature, for example, U.S. Pat. No. 10,519,146.

Example 1: Preparation of Sotorasib Form H5

Sotorasib base (500 mg) was dissolved in acetone/water/methanol 1:5:7 (45 mL) at temperature of 45° C. Obtained solution was left to cool to room temperature. At room temperature water was added to the solution, in fractions of 2 mL, total volume of 15 mL. Crystallization occurred and obtained suspension was left to stir overnight on room temperature. Next day suspension was filtered off over blue ribbon filter paper, under vacuum. Obtained solid was dried in oven on 70° C. for four hours and then analyzed by XRPD. Sotorasib Form H5 was obtained.

Example 2: Preparation of Sotorasib from Compound X 1.0 g (1.68 mmol) of X was charged in a round bottom flask, suspended in 4.0 mL (4 volumes) of acetonitrile (ACN), 387 μL (2.93 mmol) of 7.57 M aqueous potassium hydroxide solution was added and the reaction mixture dissolved from a yellow suspension into a red solution within 5 minutes. The mixture was stirred for 14 hours on ambient conditions and 8.0 mL (8 volumes) of methanol were added. pH value was adjusted to 6.6 using 1.5 mL (1.50 mmol) of 1 M aqueous phosphoric acid. The inorganics crystallized and were dissolved by heating the mixture to 45° C. and dropwise addition of 9.0 mL (9 volumes) of distilled water. The clear light yellow solution was then seeded with Compound I seed. The mixture was stirred for one hour at 45° C., cooled to room temperature and stirred for another hour. Another 7.0 mL (7 volumes) of distilled water were added dropwise and the mixture was stirred for one hour before being cooled to 0-5° C. and stirred for 1.5 hours. The white suspension was then filtered and washed two times with 2.0 mL (2 volumes) of distilled water. The white crystals were dried for 4 hours at 70° C. and 0.914 g of Compound I (Form H5) was obtained (yield=93%; assay=95.13%, chrom. purity=99.52%; chiral purity=99.93%)

Example 3: Preparation of Sotorasib from Compound X 3.0 g (5.03 mmol) of X was charged in a round bottom flask, suspended in 30.0 mL (10 volumes) of acetonitrile, 1.16 mL (8.79 mmol) of 7.57 M aqueous potassium hydroxide solution was added and the reaction mixture dissolved from a yellow suspension into a red solution within 5 minutes. The mixture as stirred for 17 hours on ambient conditions and pH value was adjusted to 6.6 using 2.4 mL (2.40 mmol) of 1 M aqueous phosphoric acid. Acetonitrile was evaporated under reduced pressure on a rotary evaporator until 4 volumes of acetonitrile remained. 24.0 mL (8 volumes) of methanol were added and the mixture was heated to 45° C. pH was adjusted to 6.6 again using 0.8 mL (0.8 mmol) of 1 M aqueous phosphoric acid. The mixture crystallized and was then dissolved by dropwise addition of 31.7 mL (10.6 volumes) of distilled water. The clear light yellow solution was then seeded with Compound I seed. The mixture was stirred for one hour at 45° C., cooled to room temperature and stirred for another hour. Another 18.0 mL (6 volumes) of distilled water were added dropwise and the mixture was stirred overnight at ambient conditions. The white suspension was then cooled to 0-5° C. and stirred for one hour. The suspension was then filtered and washed two times with 6.0 mL (2 volumes) of a mixture of MeOH/water=1:2. The white crystals (Form H5) were dried for 4 hours at 10 mbar and 70° C., 2.674 g of Compound I was obtained (yield=91%; assay=95.73%; chrom. purity=99.71%; chiral purity=99.97%).

Example 4: Preparation of Compound X 14.0 g (27.64 mmol) of Compound XV was charged in a 1 L reactor and suspended in 280 ml (20 volumes) of dichloromethane and 481 µl (2.76 mmol) of N,N-diisopropylethylamine was added followed by addition of 2.90 ml (30.40 mmol) of 3-chloropropionyl chloride (Compound XVII). The mixture was stirred for 8 hours at room temperature and transferred into a 500 ml Erlenmeyer flask. 70 ml (5 volumes) of distilled water were added and the pH value was adjusted to 6.6 using 1 M aqueous potassium carbonate. The layers were separated and the organic layer was evaporated to dryness using a rotary evaporator and stored for 2 days at 0° C. The evaporated residue was dissolved in 42 ml (3 volumes) of acetonitrile and the crystallized within minutes. The white suspension was stirred for one hour at RT and filtered, washed two times with 14 ml (1 volume) of acetonitrile. The white crystals of X were dried for one hour at 50° C. and 10 mbar and 13.28 g of X were obtained (yield=81%; assay=97.96%; chrom. purity=98.85%, chiral purity=99.97%).

Example 5: Preparation of Compound X 5.0 g (9.87 mmol) of Compound XV was charged in a 100 ml three necked flask and suspended in 25 ml (5 volumes) of N-methyl-2-pyrrolidone and 860 µl (4.94 mmol) of N,N-diisopropylethylamine was added followed by dropwise addition of 1.41 ml (14.81 mmol) of 3-chloropropionyl chloride (Compound XVII) via a peristaltic pump in the duration of 20 minutes. The mixture was stirred for 30 minutes and 12.5 ml (2.5 volumes) of distilled water were added and the pH value was adjusted to 6.6 using 4.2 ml (4.2 mmol) of 1 M aqueous potassium carbonate. The yellow solution was heated to 60° C. and 17.3 ml (3.46 volumes) of distilled water were added, spontaneous crystallization occurred. The off-white suspension was stirred for one hour at 60° C. before being cooled to room temperature and another 1.0 ml (0.2 volumes) of water was added before being stirred for one hour at room temperature. The off-white suspension was then filtered and washed two times with 25 ml (5 volumes) of water. The white crystals of X were dried for 10 hours at 50° C. and 10 mbar and 5.42 g of x were obtained. (yield=90%; assay=95.19%; chrom. purity=98.50%, chiral purity=99.86%).

The invention claimed is:

1. A crystalline form of Sotorasib, designated Form H5 which is characterized by data selected from one or more of the following:

(i) an X-ray powder diffraction pattern having peaks at: 4.4, 5.3 and 7.6 degrees 2-theta±0.2 degrees 2-theta;

(ii) an X-ray powder diffraction pattern substantially as depicted in FIG. 1;

(iii) a solid state $^{13}$C NMR spectrum having signals at: 11.4, 15.2, 22.1, 106.1 and 166.6±0.2 ppm;

(iv) a solid state $^{13}$C NMR spectrum having the following chemical shift absolute differences from a peak at 47.03 ppm±1 ppm of: 35.6, 31.8, 24.9, 59.1 and 119.6 ppm±0.1 ppm, respectively;

(v) a solid state $^{19}$F NMR spectrum having signals at −114.1, −119.9, −126.7, and −131.8±0.2 ppm; and (vi) the following unit cell parameters at 293K:

| | |
|---|---|
| Cell length a | 7.304(1) Å |
| Cell length b | 25.032(3) Å |
| Cell length c | 33.233(3) Å |
| Cell angle alpha | 90° |
| Cell angle beta | 90° |
| Cell angle gamma | 90° |
| Cell volume | 6076(1) Å$^3$ |
| Symmetry cell setting | Orthorhombic |
| Symmetry space group | P $2_12_12_1$. |

2. The crystalline form according to claim 1, which is characterized by: an X-ray powder diffraction pattern having peaks at: 4.4, 5.3 and 7.6 degrees 2-theta±0.2 degrees 2-theta, and also having any one, two, three, four, five, six or seven additional peaks selected from: 6.4, 10.7, 16.4, 18.0, 19.0, 19.5 and 21.3 degrees 2-theta±0.2 degrees 2-theta; or an X-ray powder diffraction pattern having peaks at: 4.4, 5.3, 6.4, 7.6, 10.7, 16.4, 18.0, 19.0, 19.5, and 21.3 degrees 2-theta±0.2 degrees 2-theta.

3. The crystalline form according to claim 1, which is isolated.

4. The crystalline form according to claim 1, which is a hydrate.

5. The crystalline form according to claim 1, wherein the crystalline form contains no more than about 20% of any other crystalline forms of Sotorasib.

6. The crystalline form according to claim 1, which contains no more than about 20% of amorphous Sotorasib.

7. The crystalline form according to claim 1, which is atropisomerically pure.

8. The crystalline form according to claim 1, which is (M)-Sotorasib.

9. The crystalline form according to claim 8, which is atropisomerically pure and is substantially free of (P)-Sotorasib.

10. The crystalline form according to claim 9, which contains about 0.5% (w/w) or less of (P)-Sotorasib.

11. A solid pharmaceutical composition comprising the crystalline form according to claim 1 and at least one pharmaceutically acceptable excipient.

12. A process for preparing a pharmaceutical composition comprising combining a crystalline form according to claim 1, with at least one pharmaceutically acceptable excipient.

13. A solid medicament comprising the crystalline form according to claim 1.

14. A method for treating a cancer associated with KRAS mutation including at least one of colorectal cancer, pancreatic cancer, appendiceal cancer, endometrial cancer, or melanoma, comprising administering the crystalline form according to claim 1 to a patient in need of treatment.

* * * * *